US00PP25001P2

(12) United States Plant Patent
Wijsman

(10) Patent No.: US PP25,001 P2
(45) Date of Patent: Oct. 21, 2014

(54) ***LAVANDULA* PLANT NAMED 'WIJS02'**

(50) Latin Name: ***Lavandula stoechas* spp. *lusitanica***
Varietal Denomination: Wijs02

(71) Applicant: Robert Wijsman, Boskoop (NL)

(72) Inventor: Robert Wijsman, Boskoop (NL)

( * ) Notice: Subject to any disclaimer, the term of this patent is extended or adjusted under 35 U.S.C. 154(b) by 100 days.

(21) Appl. No.: 13/815,374

(22) Filed: Feb. 26, 2013

(51) Int. Cl.
*A01H 5/00* (2006.01)

(52) U.S. Cl.
USPC ..... Plt./445

(58) Field of Classification Search
USPC ..... Plt./445
See application file for complete search history.

*Primary Examiner* — Annette Para
(74) *Attorney, Agent, or Firm* — Penny J. Aguirre

(57) ABSTRACT

A new cultivar of *Lavandula stoechas*, 'Wijs02', characterized by its inflorescences with fertile flowers that are purple-blue in color and sterile bracts that are pink in color, its good resistance to mildew, its uniform growth habit, and its late comencing and long blooming habit, and its good retention of inflorescence color after transportation without light.

2 Drawing Sheets

Botanical classification: *Lavandula stoechas* ssp. *lusitanica*.

Variety denomination: 'Wijs02'.

BACKGROUND OF THE INVENTION

The present invention relates to a new and distinct cultivar of *Lavandula stoechas* ssp. *lusitanica* will be referred to hereafter by its cultivar name, 'Wijs02'. 'Wijs02' is a new variety of lavender suitable for landscape and container use.

The inventor discovered the new cultivar, 'Wijs02', as a naturally occurring whole plant mutation in a seedbed at his nursery in Boskoop, the Netherlands in 2010. The seedbed had been planted with seeds collected from an unnamed plant of *Lavandula stoechas* ssp. *lusitanica*. The male parent is unknown.

The new cultivar was first asexually propagated by stem cuttings in Boskoop, the Netherlands in August of 2010. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new lavender. These attributes in combination distinguish 'Wijs02' as a unique cultivar of lavender.

1. 'Wijs02' exhibits inflorescences with fertile flowers that are purple-blue in color and sterile bracts that are pink in color.
2. 'Wijs02' exhibits good resistance to mildew.
3. 'Wijs02' exhibits a uniform growth habit.
4. 'Wijs02' flowers later and for a longer period than is typical of plants of *Lavandula stoechas*; from late May/early June until Late October/early November in The Netherlands.
5. 'Wijs02' exhibits inflorescenses with good retention of color after transportation without light (a frequent problem with cultivars of *Lavandula stoechas*).

The parent plant, an unnamed plant of *Lavandula stoechas* ssp. *lusitanica*, differs from 'Wijs02' in having inflorescences with purple sterile bracts rather than pink. 'Wijs02' can be most closely compared to the cultivar 'Lusi Purple' (not patented), which differs from 'Wijs02' in having inflorescences with dark purple fertile flowers and light purple sterile bracts. There are no other cultivars of *Lavandula stoechas* ssp. *lusitanica* known to the Inventor.

BRIEF DESCRIPTION OF THE DRAWING

The accompanying colored photographs illustrate the overall appearance and distinct characteristics of the new cultivar. The photographs were taken of a 10-month-old plant of the new cultivar as grown outdoors in a 17-cm container in Boskoop, The Netherlands.

The photograph in FIG. 1 illustrates a side view of 'Wijs02' in bloom.

Figure 1:
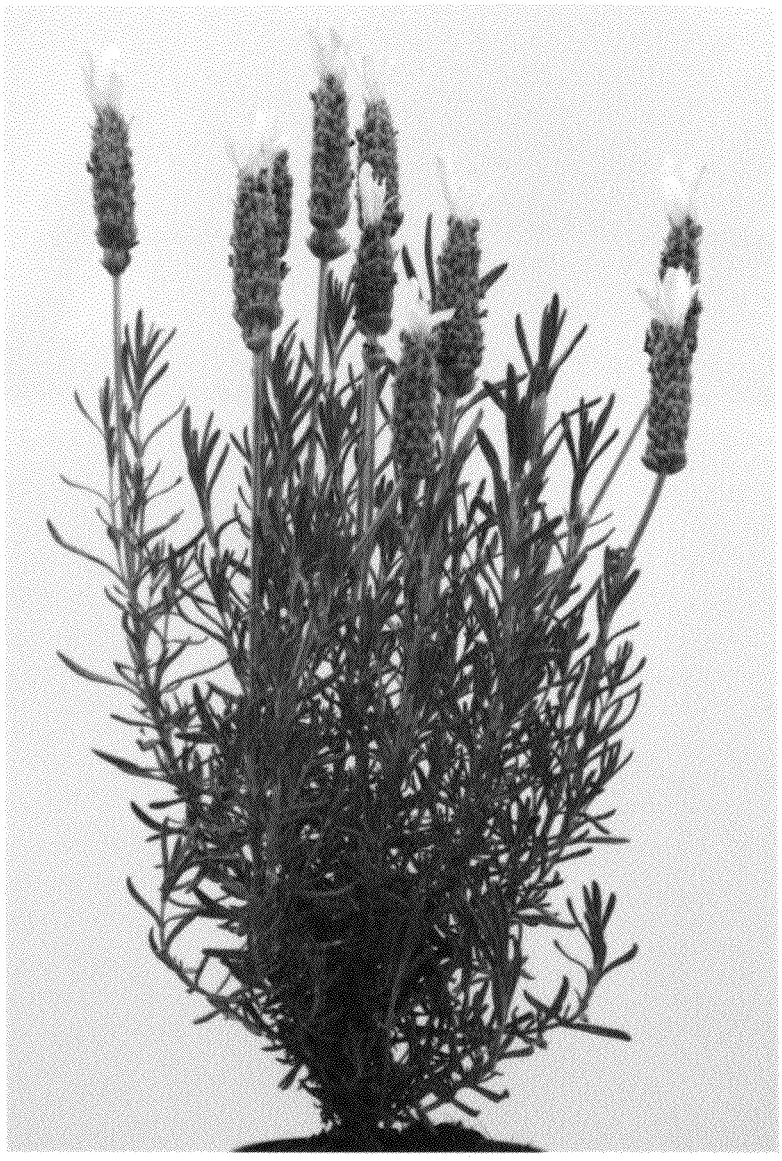
Figure 2:
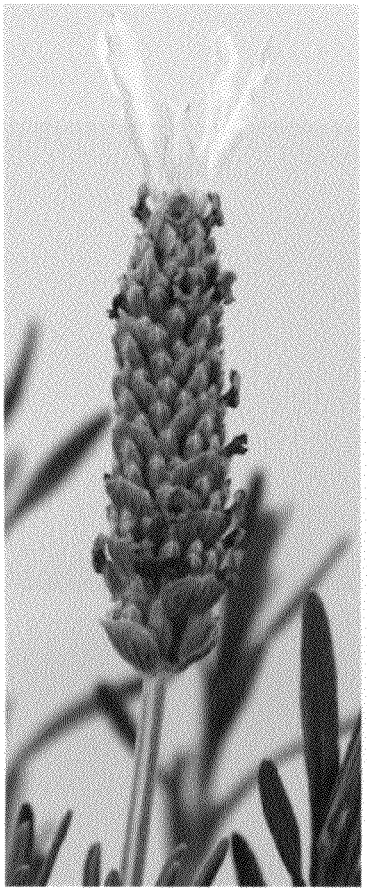

The photograph in FIG. 2 provides a close-up view of an inflorescence of 'Wijs02'.

Figure 3:
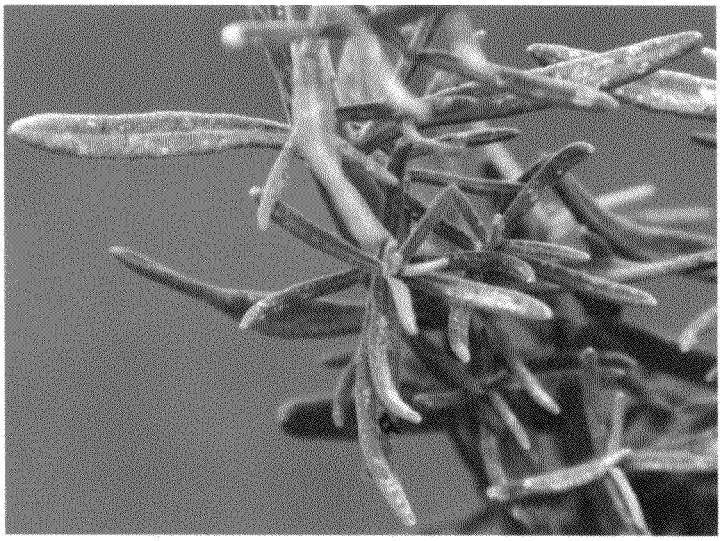

The photograph in FIG. 3 provides a close-up view of a leaf of 'Wijs02'.

The photographs are as close as possible with the digital photography techniques utilized and the color values cited in the detailed botanical description accurately describe the colors of the new lavender.

DETAILED BOTANICAL DESCRIPTION

The following is a detailed description of 10 month-old plants of the new cultivar as grown outdoors in 17-cm containers in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—Late to commence and long blooming; late May/early June until late October/early November in The Netherlands.

*Plant type.*—Perennial herb.

*Plant habit.*—Dense columnar form with upright lateral branches, uniform.

*Height and spread.*—Reaches about 42.6 cm in height and 20.9 cm in spread.

*Cold hardiness.*—At least to U.S.D A. Zone 7.

*Diseases and pests.*—Has shown good resistance to mildew.

*Root description.*—Densely fibrous, freely branched.

*Propagation.*—Stem cuttings.

*Growth.*—Moderately vigorous, grows approximately 8 cm per month in the spring.

Stem description:

*Stem shape.*—Quadangular.

*Stem color.*—144B.

*Stem surface.*—Dull and densely covered with woolly tomentose hairs about 0.2 mm in length and 145C to 145D in color.

*Stem size.*—Average of 15.1 cm in length and 2.5 mm in diameter.

*Stem strength.*—Strong.

*Branching.*—Freely branched with lateral branches emerging near the base of the main stems rather than from axillary nodes, average of 19 lateral branches on a plant developed in a 17-cm container.

Foliage description:

*Leaf shape.*—Linear, revolute.

*Leaf division.*—Simple.

*Leaf base.*—Cuneate.

*Leaf apex.*—Acute.

*Leaf venation.*—Pinnate, upper side 194C to 194D in color, lower side 147B in color.

*Leaf margins.*—Revolute, entire.

*Leaf arrangement.*—Opposite.

*Leaf attachment.*—Sessile.

*Leaf number.*—Average of 22 (11 pairs) per lateral branch.

*Leaf surface.*—Upper surface and lower surface; dull and densely covered with woolly tomentose hairs about 0.2 mm in length and 193D in color.

*Leaf size.*—Average of 2.9 cm in length and 0.35 cm in width.

*Leaf internode length.*—Average of 0.9 cm in length.

*Leaf color.*—Young upper surface; 138A, young lower surface; 147B, mature upper surface; 138A, mature lower surface; 147B.

*Leaf fragrance.*—Strongly fragrant, typical *Lavandula* scent.

Inflorescence description:

*Inflorescence type.*—Small flowers arranged in compact terminal verticillasters with showy terminal sterile bracts.

*Inflorescence number.*—1 per lateral stem.

*Inflorescence fragrance.*—None.

*Lastingness of inflorescence.*—Average of 10 days.

*Inflorescence size.*—Average of 6.7 cm in (height) and 1.4 cm in width.

*Flowers.*—Outward aspect, self-cleaning, salverform in shape, with one upper lip (split into two identical lobes) and one lower lip (split into three lobes, identical to upper lip lobes) since the lobes are identical, they are described as petals, 3.5 mm in diameter and 8 mm in depth, average of 150 flowers per inflorescence.

*Flower buds.*—Average of 7 mm in length and 2 mm in diameter, oblong in shape, color is between 152B and 197B, base is 145C.

*Petals.*—Dull and smooth, rotate in arrangement, 2 (upper lip split in 2 lobes, lower lip split in 3 lobes; all lobes are identical in shape and colour), spathulate in shape, lower 85% of petals are fused into tube, entire margin, apexes are rounded, length of petal is 8 mm, width of upper lip is 3 mm, width of lower lip is 3.5 mm, color: upper and lower surface of petal when opening and fully opened; 86B, tube is N155A, base is 158D.

*Sepals.*—Linear in shape and fused into campanulate tube, entire magin, acute apex, fused base, 6 mm in length and 1 mm in width, both surfaces are smooth and very densely covered with woolly tomentose hair, 0.2 mm in length and 190C to 190D in color, mature upper and lower surfaces are 145B in color, immature upper surface 146D in color, striped 146A to 146B, immature lower surface between 152B and 197B, base 145C, mature upper surface 146D, striped 146A to 146B, mature lower surface 197B, base 145B.

*Calyx.*—Campanulate in shape, 6 mm in length and 2 mm in diameter.

*Peduncles.*—Strong, average of 9.8 cm in length and 2 mm in diameter, held at an average angle of 0° (straight on top of lateral branch), 144B in color and densely covered with woolly tomentose pubescence, 145A to 145B in color.

*Pedicels.*—Individual flowers are sessile.

*Bracts.*—Fertile; broad rhomboidal in shape, entire margins, aristate apex, cuneate base, average of 7 mm in length and 5 mm in width, both surfaces; dull, 65D in color, veins 146A in color, densely covered with woolly tomentose, hairs less than 0.2 mm long and same color as the bract, Sterile; narrow lanceolate in shape, slightly wavy margins, broad apex, cuneate base, average of 2.1 cm in length and 5 mm in width, both surfaces; 76B in color.

Reproductive organs:

*Pistils.*—1, pistil is 4 mm in length, stigma is narrow, club-shaped and N186A in color, style is 3.5 mm in length and 155C in color, ovary is 143B in color.

*Stamens.*—4, anthers are dorsifixed and kidney-shaped and about 0.5 mm in length and 85D in color, the filament is implanted in petal and 1.5 mm in length, pollen is low and 22A in color.

*Fruit and seeds.*—No fruit or seed development has been observed under the trial conditions.

It is claimed:

1. A new and distinct cultivar of *Lavandula* plant named 'Wijs02' as herein illustrated and described.

* * * * *